United States Patent [19]

Ojima et al.

[11] Patent Number: 5,716,359
[45] Date of Patent: Feb. 10, 1998

[54] ANCHOR AND METHOD FOR FIXING A SCREW IN BONE

[75] Inventors: Satoshi Ojima; Masahiro Kohketsu, both of Tokyo, Japan

[73] Assignee: Asahi Kogaku Kogyo Kabushiki Kaisha, Tokyo, Japan

[21] Appl. No.: 654,876

[22] Filed: May 29, 1996

[30] Foreign Application Priority Data

May 30, 1995 [JP] Japan .................... 7-131879

[51] Int. Cl.⁶ .................................... A61B 17/58
[52] U.S. Cl. ................ 606/76; 606/72; 606/73; 606/77
[58] Field of Search .............. 606/76, 77, 72, 606/104, 73

[56] References Cited

U.S. PATENT DOCUMENTS

| | | |
|---|---|---|
| 4,778,471 | 10/1988 | Bajpai .................... 623/16 |
| 4,798,585 | 1/1989 | Inoue et al. . |
| 4,969,913 | 11/1990 | Ojima . |
| 5,017,518 | 5/1991 | Hirayama et al. . |
| 5,064,436 | 11/1991 | Ogiso et al. . |
| 5,084,050 | 1/1992 | Draenert . |
| 5,147,361 | 9/1992 | Ojima et al. . |
| 5,149,368 | 9/1992 | Liu et al. .................... 424/602 |

FOREIGN PATENT DOCUMENTS 2237564  5/1991  United Kingdom .

*Primary Examiner*—Michael Buiz
*Assistant Examiner*—Julian W. Woo
*Attorney, Agent, or Firm*—Greenblum & Bernstein, P.L.C.

[57] ABSTRACT

An anchor including a shank formed from a hardened product of a calcium phosphate compound. The anchor having a strength capable of retaining its original shape, before, during and after insertion into a pre-drilled hole of a bone, and a brittleness capable of causing its original shape to disintegrate as a result of a breakage of the shank upon an application of a driving force from the screw to the shank during a driving of the screw through the anchor inserted in the bone. The present invention also relates to a method for fixing a screw in a bone. Using the anchor of the present invention, it becomes possible to easily and reliably fix a screw in a bone having a reduced strength.

17 Claims, 3 Drawing Sheets

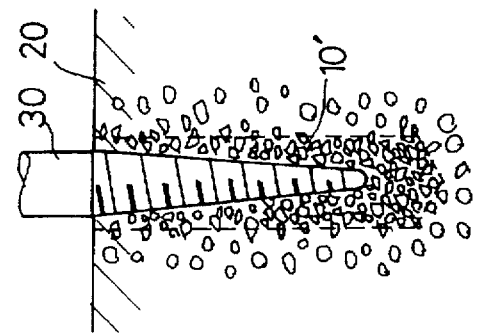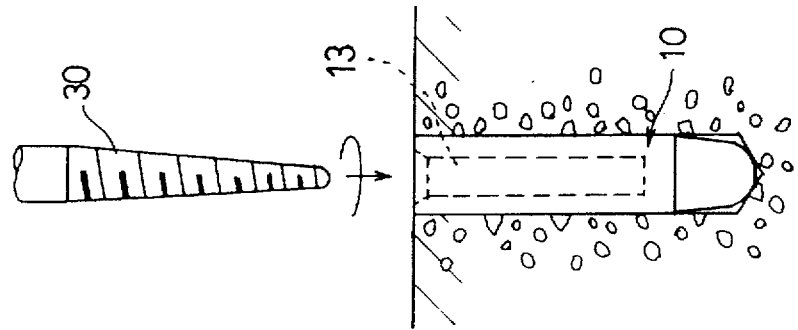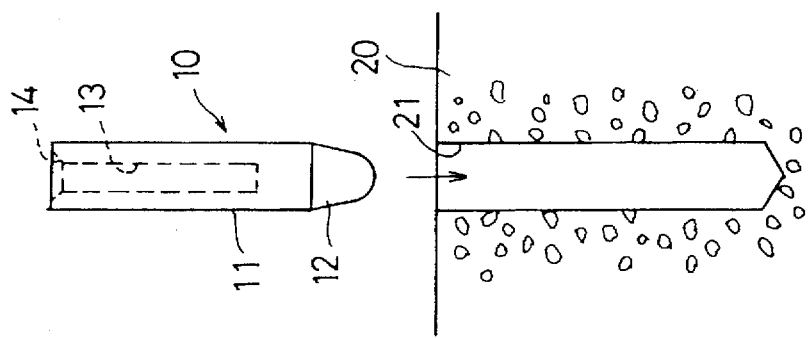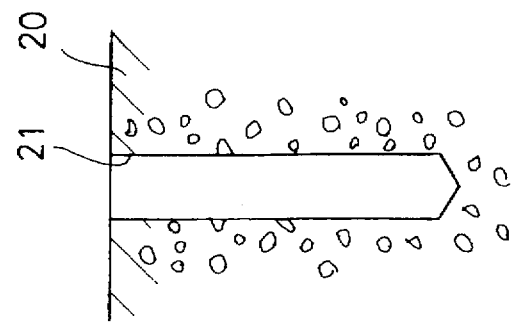

ANCHOR AND METHOD FOR FIXING A SCREW IN BONE

BACKGROUND OF THE INVENTION

1. Field of the Invention

The present invention relates to an anchoring element and method for fixing a screw in bone. More particularly, the present invention relates to an anchoring element for use in driving and fixing a screw, bolt or other part into bone. The present invention also relates to a method for fixedly securing a screw in the bone.

2. Description of the Related Art

It is widely known to use screws, bolts or other parts (hereinafter referred to as a "screw") in osteopathy or in the treatment of various bone diseases, such as the deformation or fracture of bones in humans and animals. For example, in often performing osteopathy a screw is driven and fixed in a predetermined site of a bone during an operation. If the bone has a sufficiently high strength, the screw can be directly driven into the predetermined site, or alternatively can be inserted and driven into a hole, after first drilling the hole in the bone for the purpose of easy insertion of the screw in the bone. After the screw has been fixed, a sufficiently high bonding strength can be thus obtained between the bone and the screw driven therein.

However, it is difficult to drive screws into the bones of patients suffering from osteoporosis, since finely distributed pores in the bone result in a poor fixing strength between the bone and screw.

Problems resulting from poor fixing strength will become apparent from the example of postspinal fusion which will now be described below.

Postspinal fusion comprises driving a screw into multiple bones (bodies) (i.e. vertebra) and fixedly attaching the driven screws to a curing or corrective plate positioned over two or more vertically adjacent bones. However, if the resulting bonding strength between the bone and screw is poor, satisfactory curing effects cannot be accomplished after this operation. Consequently in some cases, the operation itself can not be applied to certain patients. In order to avoid this problem, attempts have been previously made to drill a hole in the bone, and then drive a screw into the pre-drilled hole, after first filling the hole with an artificial bone material, such as particulate apatite, paste-like calcium phosphate cement, or the like. However, the step of filling the particulate or paste-like material in the hole is time-consuming and reduces workability, in addition, it is also difficult to exactly fill the pre-drilled hole with an exact amount of artificial bonematerial.

SUMMARY OF THE INVENTION

The present invention is directed to solving the above-mentioned problems involved in driving and fixing a screw into a bone, and particularly the problem of having a reduced fixing strength between a bone and a screw observed when the screw is driven into a bone having a reduced strength such as the the bone of a patient suffering from osteoporosis.

It is therefore an object of the present invention to provide an anchor which enables an easy and reliable insertion and fixation of a screw into a weakened portion of a bone.

Another object of the present invention is to provide a method of driving and securing a screw into a bone using the anchor of the present invention.

In one aspect of the present invention, there is provided an anchor to be inserted into a pre-drilled hole of a bone, to thereby assist a fixation of a screw in the bone. The anchor includes a shank made from a hardened product of a calcium phosphate compound, having a strength capable of retaining its original shape, before, during and after insertion into the pre-drilled hole, and a brittleness capable of causing its original shape to disintegrate as a result of a breakage of the shank upon an application of a driving force from the screw to the shank when the screw is driven through the anchor inserted in the bone.

In another aspect of the present invention, there is provided a method of fixing a screw in a bone, comprising the steps of firstly, drilling a hole in a predetermined site of the bone, and secondly inserting an anchor into the pre-drilled bone hole. The anchor includes a shank made from a hardened product of a calcium phosphate compound, having a strength capable of retaining its original shape, before, during and after insertion into the pre-drilled hole, and a brittleness capable of causing its original shape to disintegrate as a result of a breakage of the shank upon an application of a driving force from the screw to the shank when the screw is driven through the anchor inserted in the bone. Thirdly, a screw is driven through the anchor inserted in the bone.

Since the anchor of the present invention can retain its original shape before insertion into the bone, the anchor can easily be inserted into a hole previously drilled in the bone, and after inserting the anchor into the hole in the bone and subsequently driving a screw into the anchor, the inserted anchor can be broken to such an extent that the original shape of the anchor disintegrates, thereby causing a distribution of the resulting finely divided anchor material in a gap created by the screw and the bone hole. The finely divided anchor material can act to securely and strongly fix the driven screw against the bone. Therefore, the anchor of the present invention can be widely and advantageously used in the treatment of bone diseases which include the step of driving a screw into the bone. Particularly, the anchor of the present invention can be effectively applied to an orthopedic operation in which the bone, in which the anchor is to be driven into does not have a sufficiently high strength, such as the bone of a patient suffering from osteoporosis.

The present disclosure relates to subject matter contained in the Japanese Patent Application No. 07-131879 (filed on May 30, 1995) which is expressly incorporated herein by reference in its entirety.

BRIEF DESCRIPTION OF THE DRAWINGS

The present invention will be more clearly understood from the description as set forth below with reference to the accompanying drawings, in which like parts are indicated by similar reference numerals, and wherein:

FIGS. 3A to 3D are cross-sectional views showing, in sequence, a screw being fixed into a bone using the anchor according to the present invention;

DESCRIPTION OF THE PREFERRED EMBODIMENTS

Figure 1:
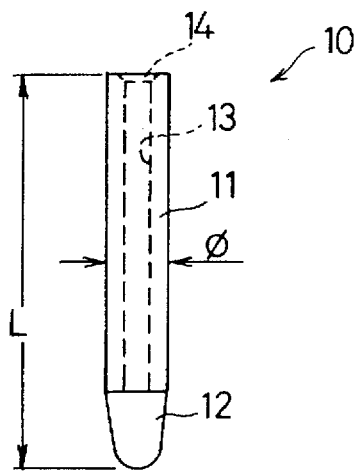
FIG. 1 is a front view of an anchor for fixing a screw in the bone, according to a preferred embodiment of the present invention.

An anchor element (hereinafter referred to as an "anchor") according to an aspect of the present invention comprises a shank which is made from a hardened product of a calcium phosphate compound. Furthermore, the strength of the shank is such that it is capable of retaining its original shape, before, during and after insertion of the anchor into a pre-drilled hole in a bone, and in addition, the shank has a brittleness such as to cause the original shape to disintegrate as a result of a breakage of the shank upon an application of a driving force of a screw to the shank when the screw is driven through the anchor inserted into the bone.

When the anchor of the present invention is used in a fixing operation of a screw to a bone, the anchor can be easily and reliably inserted in a pre-drilled hole of the bone, and, after its insertion can be finely broken by a driving force of the screw when the screw is driven through the anchor inserted in the bone. Then, the finely broken anchor material, i.e., powder-like calcium phosphate compound, can be uniformly distributed around an outer surface of the driven screw, thereby ensuring fixation of the screw to the bone with a highly increased bonding strength.

In the anchor of the present invention, the shank may have any desired size, shape or configuration in conformity with the hole drilled in the bone. Generally, it is preferred that the shank has a diameter and length which is substantially the same as that of the pre-drilled bone hole, although the diameter and length of the shank may vary widely depending upon a variety of factors. Further, from practical use of the anchor, it is preferred that the shank is constituted as having a column-shaped body, since the pre-drilled bone hole is generally opened by using a drilling tool. The shank having a column-shaped body may have any desired size depending upon various factors such as its insertion site, but preferably the column-shaped shank has a diameter of about 1.5 to 5.0mm and a length of about 15 to 60mm.

The column-shaped shank, and other forms of shank discussed in the present invention, may have either a solid body or a hollow body with a hole for receiving a screw therein. When the shank has a screw-receiving hole bored therein, it is preferred that the hole has a diameter of about 0.5 to 3.5mm and a depth or length of at least one about third of the full length of the shank, preferably at least about one half of the full length of the shank.

In the anchor according to the present invention, the shank thereof is made from a calcium phosphate compound, and in order to obtain a desired balance of strength and brittleness, as well as a good biocompatibility, it is preferred that the calcium phosphate compound has a molar ratio of Ca/P of about 1.5 to 2.0. Suitable calcium phosphate compounds include, for example, a variety of apatites such as hydroxyapatite, fluoroapatite and the like, tricalcium phosphate, tetracalcium phosphate and other calcium phosphates. These calcium phosphate compounds may be used alone or in a mixture of two or more phosphate compounds.

In the practice of the present invention, the calcium phosphate compound is hardened to form a hardened product having a size and configuration corresponding to those of the desired anchor. More particularly, the calcium phosphate compound may be sintered in accordance with any conventional method to obtain a sintered product thereof. Preferably, the sintered product of the calcium phosphate compound has a porosity of about 40 to 80%. A sintered product having a porosity of less than about 40% should be avoided, because it does not ensure that the shank has a sufficient strength. On the other hand, a porosity above about 80% does not ensure a required brittleness of the shank.

Alternatively, the calcium phosphate compound may be molded in accordance with any conventional method to obtain a molded product having a configuration and size corresponding to those of the desired anchor. For example, the molding may be carried out by using a hydraulic calcium phosphate as a starting material. After molding thereof to obtain a desired configuration and size, the hydraulic calcium phosphate can be hardened in the presence of water. Preferably, the molded product of the calcium phosphate compound has a porosity of about 20 to 70%. A porosity of less than about 20% should be avoided in the molded product, because it does not ensure the required strength of the shank. On the other hand, a porosity greater than about 70% does not ensure the required brittleness of the shank.

The method of production of the anchor of the present invention is not restricted, and can be produced by using any conventional method, for example, using hydroxyapatite as a starting material, the anchor, in the form of a sintered product, can be produced in accordance with the following manner:

Firstly, a slurry of hydroxyapatite is produced, from phosphoric acid and calcium salt compounds, to be used as the starting materials in a conventional wet process. The resulting slurry is then dried in a rotary drum-type dryer to obtain hydroxyapatite in powder form. The hydroxyapatite powder is then molded in a conventional molding apparatus, such as a dry-type hydrostatic press, to obtain a hydroxyapatite molded product having a configuration corresponding to that of the intended anchor. After molding is complete, the molded product is calcined at a temperature of about 1000° to 1200° C. in an electric oven, and thus the anchor of the present invention is produced.

In the above-mentioned production process, a dry-type hydrostatic press was used as the molding apparatus, however, it will be appreciated that any other molding apparatus or method can be freely used in the practice of the present invention. Suitable molding methods include, for example, cast molding, injection molding, lathing of the press-molded powders and the like.

Further, the anchor of the present invention can be produced by using α-tricalcium phosphate as a starting material. The α-tricalcium phosphate is blended and kneaded with water, which may, if desired, contain an acid to act as a solidifying agent, to produce a hardened product. The hardened product is then fabricated to obtain a configuration corresponding to that of the intended anchor. Alternatively, the fabrication process may be omitted, with the hardened product being produced in a suitable mold by kneading the α-tricalcium phosphate and water mixture in the mold.

The anchor according to the present invention can be advantageously and effectively used as an assisting means in the driving and fixing of a screw to a bone, particularly the bone of humans or animals. The method of fixing a screw in a bone using the anchor of the present invention comprises the step of drilling a hole in a predetermined site of the bone. After formation of the pre-drilled hole, the anchor of the present invention, namely, the anchor comprising a shank made from a hardened product of calcium phosphate compound, in which the shank has a strength capable of retaining its original shape, before, during and after insertion into the pre-drilled hole, and a brittleness capable of causing the original shape to disintegrate as a result of a breakage of the shank upon application of a driving force of the screw to the shank when the screw is driven through the anchor inserted in the bone, is inserted in the pre-drilled bone hole in any conventional manner. Then, a screw is driven through the anchor by using any conventional manner.

The present invention will now be further described, with the aid of the attached diagrams, with reference to some preferred examples of the present anchor. Note however, that the present invention should not be restricted to these examples.

Figure 2:
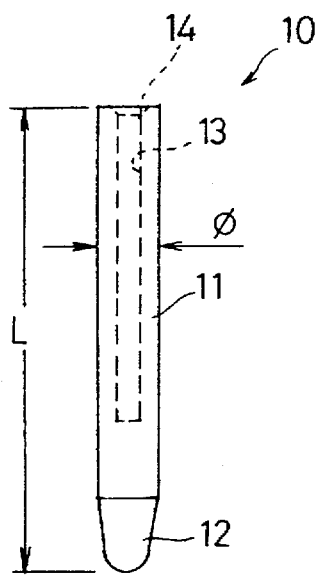
FIG. 2 is a front view of another anchor for fixing a screw in the bone, according to another embodiment of the present invention.

FIGS. 1 and 2 each illustrate a typical example of an anchor 10 according to the present invention. The anchor 10 comprises a column-shaped shank 11, and a tip portion 12 extending from the column-shaped shank 11. The tip portion 12, as is illustrated, has a tapered configuration, namely, a gradually reducing diameter, for the purpose of ensuring easy insertion of the anchor 10 into a pre-drilled bone hole. Further, the column-shaped shank 11 contains a screw-receiving hole 13 for receiving a screw when the screw is driven in the pre-drilled bone hole. The screw-receiving hole 13, as is illustrated, has an opened end with a bevel 14, along with a closed end at the vicinity of the boundary between the column-shaped shank 11 and the tip portion 12. The anchor 10 has a length L and a diameter, which can be widely varied in order to provide a plurality of anchors having different lengths and diameters so that suitable anchors can be selected for each pre-drilled bone hole before fixation of the screw in the bone.

FIGS. 3A to 3D illustrate, in sequence, the fixation of a screw in a bone.

First, as is shown in FIG. 3A, a hole 21 for receiving the anchor 10 is made in a bone 20. A drilling tool (not shown) is used to make the hole 21.

Then, as is shown in FIG. 3B, the anchor 10, described above with reference to FIG. 2, is inserted in the pre-drilled bone hole 21. The tapered tip portion 12 is first inserted in the bone hole 21. During and after insertion thereof in the bone hole 21, the anchor 10 can retain its original shape.

After insertion of the anchor 10 in the bone hole 21, as shown in FIG. 3C, a screw 30 is inserted in the screw-receiving hole 13 of the inserted anchor 10, after a tip portion of the screw 30 has aligned with the bevel 14 of the hole 13. In the process of driving the screw 30 in the hole 13, the anchor 10 is gradually broken due to a driving force of the screw 30. The original shape of the anchor 10 thus disintegrates.

As shown in FIG. 3D, the anchor 10 is finely divided to make powder-like fragments 10' of the anchor material, which are then distributed around the driven screw 30. When the anchor 10 is broken in an initial stage of the driving of the screw 30, a substantial portion of the screw 30 can be driven into the fragments 10', after the hole 21 is filled with the fragments 10'. In this instance, since the fragments 10' can be tightly positioned between the hollow of the bone 20 and the screw 30 inserted therein, it becomes possible to strongly bond a screw 30 against the bone 20.

Figure 4:
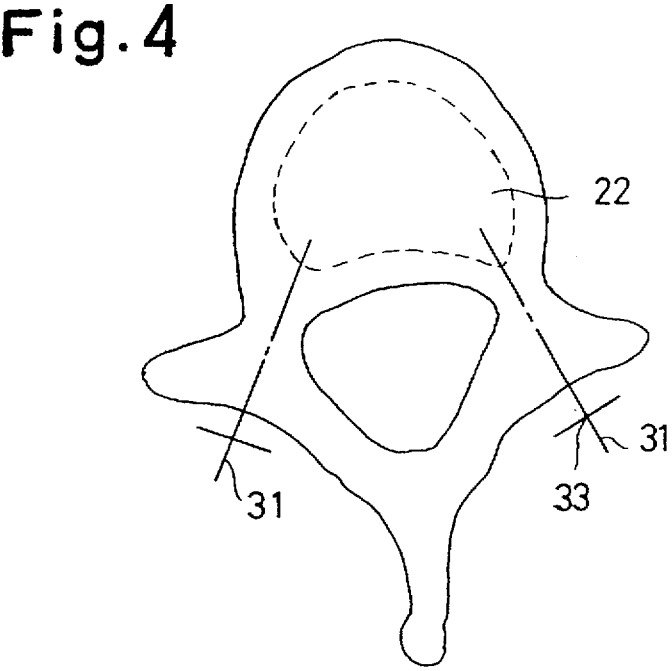
FIG. 4 is a conceptual plan view illustrating postspinal fusion using screws.
Figure 5:
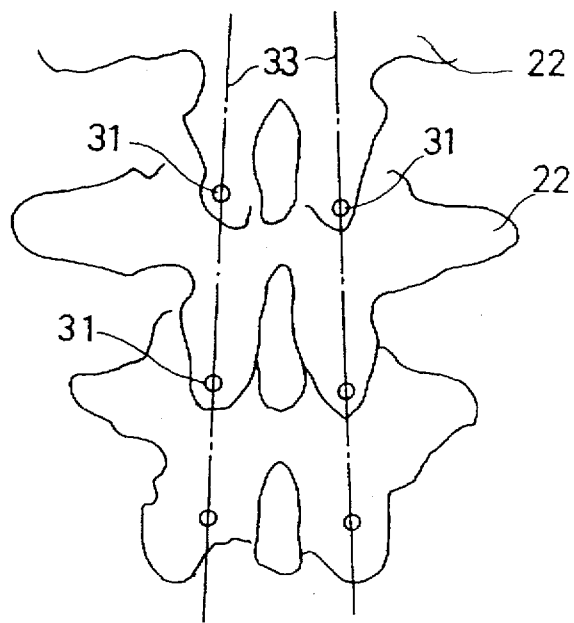
FIG. 5 is a conceptual front view also illustrating postspinal fusion using screws.

FIGS. 4 and 5 each illustrate the concept of postspinal fusion to which the anchor of the present invention can be advantageously applied. In each of upper and lower vertebral bodies 22, a screw 31, such as a pedicle screw, is driven, and then a common corrective plate 33, for the bodies of the vertebra, is attached and fixed to suitable sites of the screws 31 at outwardly extending ends thereof. The above-illustrated anchor 10 of the present invention can be used in, for example, this postspinal fusion for the purpose of driving and fixing the screws 31 in the vertebral bodies 22.

The following examples will describe the production of the above-illustrated anchor 10 according to the present invention.

EXAMPLE 1

A slurry of hydroxyapatite was produced in a conventional wet process, and was then dried by a spray dryer to obtain hydroxyapatite powders. The powders were pressed on a mold to produce a pressed powder body having a diameter of 10mm and a length of 60mm. The pressed powder body was fabricated on an NC lathe to obtain a size of 6mm in diameter, 45mm in length and 2mm in diameter at the screw-receiving hole. The above size of the lathed product was determined considering the fact that the lathed product can slightly shrink during calcination. The lathed product was then calcined at 1100° C. for 2 hours in an electric oven. The anchor illustrated in FIGS. 1 and 2 was thus produced, having a size of 4mm in diameter, 30mm in length and 1.35mm in diameter at the screw-receiving hole.

EXAMPLE 2

An aqueous solution, comprising phosphoric acid and a suspension of calcium hydroxide, were reacted and dried in accordance with a conventional method to produce hydroxyapatite having a Ca/P ratio of 1.67, which was then calcined at a temperature of 1300° C. and at a pressure of $1.3 \times 10^{-4}$ Pa for one hour. The hydroxyapatite was pyrolytically decomposed resulting in a mixture of $\alpha$-tricalcium phosphate and tetracalcium phosphate. After pulverization, the powdery mixture of $\alpha$-tricalcium phosphate and tetracalcium phosphate was blended and kneaded with an aqueous solution containing 45% of citric acid, 15% of glucose and 1% of chitosan in a powder-to-solution ratio of 2:1. The kneaded product was poured in the split molds, made of of polyacetal, provided with a bored cavity corresponding to the configuration of the intended tapered shank body, and left to harden therein for about 10 minutes. The bored cavity of the split molds had a diameter of 10mm at the narrowed end thereof and a diameter of 15mm at the widened end thereof as well as a length of 75mm. After the content of the cavity had completely hardened, the hardened product was removed from the molds having a desired column-like configuration. The hardened product was further drilled to form a screw-receiving hole having a diameter of 1.35mm. The anchor illustrated in FIGS. 1 and 2 was thus produced.

What is claimed is:

1. An anchor to be inserted into a pre-drilled hole of a bone, thereby assisting a fixation of a screw in the bone, comprising in combination:

a shank composed of hardened product of calcium phosphate compound;

said shank comprising a screw-receiving hole and having a strength capable of retaining an original shape, before, during and after insertion into said pre-drilled hole; and said shank further having a brittleness capable of causing said original shape to disintegrate as a result of a breakage of said shank upon application of a driving force from said screw to said shank when said screw is driven through said anchor inserted in the bone; and a screw, said screw comprising a portion sized to be insertable into said hole and a portion having a diameter greater than the diameter of said hole.

2. The anchor according to claim 1, wherein said calcium phosphate compound has a molar ratio of calcium to phosphorous of about 1.5 to 2.0.

3. The anchor according to claim 2, wherein said calcium phosphate compound comprises at least one member selected from a group consisting of hydroxyapatite, fluoroapatite, tricalcium phosphate and tetracalcium phosphate.

4. The anchor according to claim 3, wherein said calcium phosphate compound comprises hydroxyapatite.

5. The anchor according to claim 1, wherein said hardened product is a sintered product of said calcium phosphate compound having a porosity of about 40 to 80%.

6. The anchor according to claim 1, wherein said hardened product is a molded product of said calcium phosphate compound having a porosity of about 20 to 70%.

7. The method according to claim 5, wherein said shank has a diameter and a length substantially the same as that of said pre-drilled hole in the bone.

8. The anchor according to claim 5, wherein said shank is a column-shaped body having a diameter of about 1.5 to 5.0 mm and a length of about 15 to 60 mm.

9. The anchor according to claim 8, wherein said screw-receiving hole is bored in said column-shaped body.

10. The anchor according to claim 1, said anchor being used to drive and fix a screw in a weakened portion of a bone of a patient suffering from osteoporosis.

11. A method of fixing a screw in a bone, comprising:

drilling a hole in a predetermined site in the bone;
inserting an anchor into said pre-drilled hole, wherein said anchor comprises a shank composed of hardened product of calcium phosphate compound, said shank having a strength capable of retaining an original shape, before, during and after insertion into said pre-drilled hole, said shank also having a brittleness capable of causing said original shape to disintegrate as a result of a breakage of said shank upon application of a driving force from said screw to said shank when said screw is driven through said anchor inserted in the bone; and driving said screw through said anchor inserted in said bone to disintegrate said anchor.

12. The method according to claim 11, wherein said hardened product is a sintered product of said calcium phosphate compound having a porosity of about 40 to 80%.

13. The method according to claim 11, wherein said hardened product is a molded product of said calcium phosphate compound having a porosity of about 20 to 70%.

14. The method according to claim 12, wherein said shank is a column-shaped body having a diameter of about 1.5 to 5.0 mm and a length of about 15 to 60 mm.

15. The method according to claim 14, wherein said column-shaped body has a screw-receiving hole bored therein.

16. The method according to claim 11, wherein said screw is driven into a weakened portion of a bone of a patient suffering from osteoporosis.

17. The method according to claim 14, wherein said column-shaped body has a screw-receiving hole therein.

* * * * *